US00PP33536P2

(12) United States Plant Patent
Lannes

(10) Patent No.: US PP33,536 P2
(45) Date of Patent: Oct. 5, 2021

(54) ***MANDEVILLA* PLANT NAMED 'LANNORTHDAKOTA'**

(50) Latin Name: *Mandevilla sanderi*
Varietal Denomination: Lannorthdakota

(71) Applicant: Robert Lannes, Malause (FR)

(72) Inventor: Robert Lannes, Malause (FR)

(73) Assignee: D.H.M. INNOVATION S.A.S., Malause (FR)

( * ) Notice: Subject to any disclaimer, the term of this patent is extended or adjusted under 35 U.S.C. 154(b) by 0 days.

(21) Appl. No.: 17/159,055

(22) Filed: Jan. 26, 2021

(51) Int. Cl.
*A01H 5/02* (2018.01)
*A01H 6/08* (2018.01)

(52) U.S. Cl.
USPC ..... Plt./232

(58) Field of Classification Search
USPC ..... Plt./232, 226
CPC ... A01H 5/02; A01H 5/00; A01H 6/08; A01H 6/088
See application file for complete search history.

(56) References Cited

PUBLICATIONS

Floral Daily 9 new varieties Diamantina series continues to expand 2020, retrieved on Apr. 8, 2021, retrieved from the Internet at https://www.floraldaily.com/article/9179401/diamantina-series-continues-to-expand/, 3 pp. (Year: 2020).*
Upov Pluto Plant Variety Database 20210406, retrieved on Apr. 8, 2021, retrieved from the Internet at https://www.upov.int/pluto/en/index.jsp, one page (Year: 2021).*

* cited by examiner

*Primary Examiner* — June Hwu
(74) *Attorney, Agent, or Firm* — C. Anne Whealy

(57) ABSTRACT

A new and distinct cultivar of *Mandevilla* plant named 'Lannorthdakota', characterized by its broadly vining plant habit; vigorous growth habit; freely branching habit; glossy dark green-colored leaves; early and freely flowering habit; and flowers with rounded red purple-colored petals and broad dark yellow-colored throats.

2 Drawing Sheets

Figure 1:
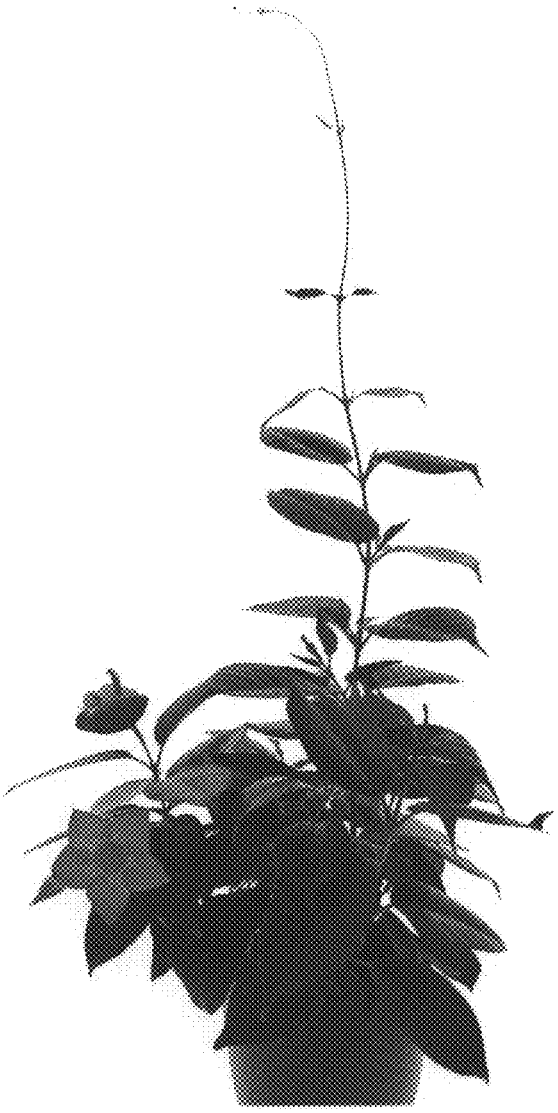

Botanical designation: *Mandevilla sanderi.*
Cultivar denomination: 'LANNORTHDAKOTA'.

STATEMENT REGARDING PRIOR DISCLOSURES BY THE INVENTOR/APPLICANT & ASSIGNEE

An European Community Plant Breeder's Rights application for the instant plant was filed by the D.H.M. Innovations S.A.S. of Malause, France on Nov. 24, 2020, application number 2020/2971. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Mandevilla* plant, botanically known as *Mandevilla sanderi* and hereinafter referred to by the name 'Lannorthdakota'.

The new *Mandevilla* plant is a product of a planned breeding program conducted by the Inventor in Malause, France. The objective of the breeding program is to create new vigorous and freely branching *Mandevilla* plants with numerous unique and attractive flowers.

The new *Mandevilla* plant originated from a cross-pollination conducted by the Inventor in Malause, France during the spring of 2016 of a proprietary selection of *Mandevilla sanderi* identified as code number si u231-0, not patented, as the female, or seed, parent with *Mandevilla sanderi* 'Lanmalause', not patented, as the male, or pollen, parent. The new *Mandevilla* plant was discovered and selected by the Inventor as a single flowering plant from within the progeny of the stated cross-pollination in a controlled greenhouse environment in Malause, France during the spring/summer of 2018.

Asexual reproduction of the new *Mandevilla* plant by cuttings in a controlled greenhouse environment in Malause, France since September, 2019 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Lannorthdakota'. These characteristics in combination distinguish 'Lannorthdakota' as a new and distinct *Mandevilla* plant:

1. Broadly vining plant habit.
2. Moderately vigorous to vigorous growth habit.
3. Freely branching habit.
4. Glossy dark green-colored leaves.
5. Early and freely flowering habit.
6. Flowers with rounded red purple-colored petals and broad dark yellow-colored throats.

Plants of the new *Mandevilla* can be compared to plants of the female parent selection. Plants of the new *Mandevilla* differ primarily from plants of the female parent selection in the following characteristics:

1. Plants of the new *Mandevilla* are more vining than and not as compact and upright as plants of the female parent selection.
2. Flowers of plants of the new *Mandevilla* have rounded red purple-colored petals and broad dark yellow-colored throats whereas flowers of plants of the female parent selection have pointed white-colored petals with narrow orange-colored throats.

Plants of the new *Mandevilla* can be compared to plants of the male parent, 'Lanmalause'. Plants of the new *Mandevilla* differ primarily from plants of 'Lanmalause' in the following characteristics:

1. Plants of the new *Mandevilla* are more vining than and not as compact as plants of 'Lanmalause'.
2. Plants of the new *Mandevilla* are more freely branching than plants of 'Lanmalause'.
3. Flower petals of plants of the new *Mandevilla* are red purple in color whereas flower petals of plants of 'Lanmalause' are red orange in color.
4. Flowers of plants of the new *Mandevilla* resist fading under high light exposure whereas flowers of 'Lanmalause' fade under high light exposure.

Plants of the new *Mandevilla* can also be compared to plants of *Mandevilla sanderi* 'Rosea Fonce', not patented. In side-by-side comparisons, plants of the new *Mandevilla* differ primarily from plants 'Rosea Fonce' in the following characteristics:

1. Plants of the new *Mandevilla* are more freely branching than plants of 'Rosea Fonce'.
2. Plants of the new *Mandevilla* flower much earlier than plants of 'Rosea Fonce'.
3. Plants of the new *Mandevilla* have larger flowers than plants of 'Rosea Fonce'.

Plants of the new *Mandevilla* can also be compared to plants of *Mandevilla sanderi* 'Sunparapibra', disclosed in U.S. Plant Pat. No. 19,649. In side-by-side comparisons, plants of the new *Mandevilla* differ primarily from plants 'Sunparapibra' in the following characteristics:

1. Plants of the new *Mandevilla* are more vining and vigorous than plants of 'Sunparapibra'.
2. Flowers of plants of the new *Mandevilla* have red purple-colored petals and broad dark yellow-colored throats whereas flowers of plants of 'Sunparapibra' have light pink-colored petals with narrow orange-colored throats.
3. Plants of the new *Mandevilla* are more resistant to fungal pathogens than plants of 'Sunparapibra'.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet (FIG. 1) comprises a side perspective view of a typical flowering plant of 'Lannorthdakota' grown in a container.

Figure 2:
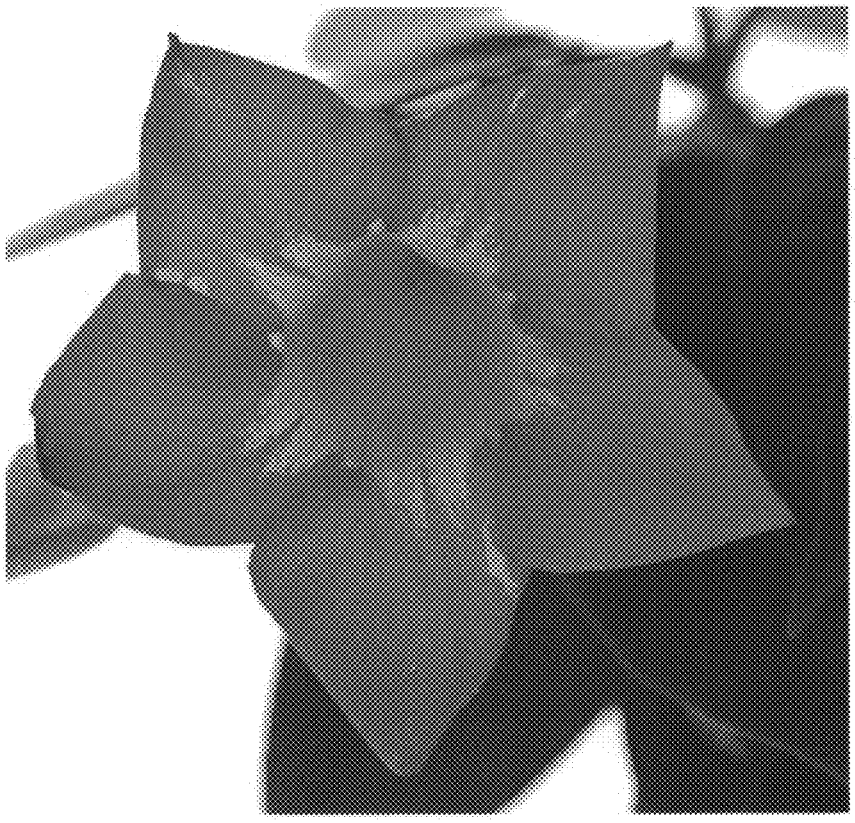

The photograph on the second sheet (FIG. 2) is a close-up view of a typical open flower of 'Lannorthdakota'.

DETAILED BOTANICAL DESCRIPTION

The aforementioned photographs and following observations, measurements and values describe plants grown during the winter and early spring in 12-cm containers in a polyethylene-covered greenhouse in Motril, Spain and under cultural practices typical of commercial *Mandevilla* production. During the production of the plants, day temperatures ranged from 15° C. to 26° C. and night temperatures ranged from 12° C. to 18° C. Plants were seven months old when the photographs and description were taken. In the following description, color references are made to The Royal Horticultural Society Colour Chart, 2015 Edition, except where general terms of ordinary dictionary significance are used.

Botanical classification:

*Mandevilla sanderi* 'Lannorthdakota'.

Parentage:

*Female, or seed, parent.*—Proprietary selection of *Mandevilla sanderi* identified as code number si u231-0, not patented.

*Male, or pollen, parent.*—*Mandevilla sanderi* 'Lanmalause', not patented.

Propagation:

*Type.*—By vegetative cuttings.

*Time to initiate roots, summer.*—About two weeks at temperatures about 23° C. to 30° C.

*Time to initiate roots, winter.*—About three weeks at temperatures about 23° C. to 25° C.

*Time to produce a rooted young plant, summer.*—About five to six weeks at temperatures about 23° C. to 30° C.

*Time to produce a rooted young plant, winter.*—About six to eight weeks at temperatures about 23° C. to 25° C.

*Root description.*—Fine, fibrous; typically light yellowish white in color, actual color of the roots is dependent on substrate composition, water quality, fertilizers, substrate temperature and physiological age of roots.

*Rooting habit.*—Freely branching; medium density.

Plant description:

*Plant and growth habit.*—Broadly vining plant habit; upright to broadly spreading; overall plant plant shape, broadly obovate; moderately vigorous to vigorous growth habit and moderate growth rate.

*Plant height, soil level to top of foliar plane.*—About 44.3 cm.

*Plant height, soil level to top of floral plane.*—About 24 cm.

*Plant diameter (spread).*—About 56.2 cm.

*Lateral branch description.*—

*Branching habit.*—Freely branching habit, about four primary lateral branches each with about two secondary lateral branches developing per plant.

*Length*.—About 41.1 cm.
*Diameter*.—About 3 mm.
*Internode length*.—About 4.5 cm.
*Aspect*.—Primary lateral branches, mostly erect; secondary lateral branches, about 25° to 45° from primary branches.
*Strength*.—Strong.
*Texture and luster*.—Smooth, glabrous; moderately glossy; becoming woody with development.
*Color, developing*.—Close to 146C.
*Color, developed*.—Close to 144A; when woody, close to N199A.

Leaf description:
*Arrangement*.—Opposite, simple.
*Length*.—About 10.4 cm.
*Width*.—About 5.9 cm.
*Shape*.—Broadly elliptic to broadly ovate and broadly obovate.
*Apex*.—Apiculate to broadly aristate.
*Base*.—Obtuse to shallowly truncate.
*Margin*.—Entire, slightly undulate.
*Texture and luster, upper and lower surfaces*.—Smooth, glabrous; not rugose; moderately coriaceous; moderately glossy.
*Venation pattern*.—Pinnate.
*Color*.—
*Developing leaves, upper surface*.—Darker than 144A.
*Developing leaves, lower surface*.—Close to 146A.
*Full expanded leaves, upper surface*.—Close to NN137B; venation, close to 144A to 144B.
*Fully expanded leaves, lower surface*.—Close to a blend of 144A and 146B; venation, close to 145B to 145C.
*Petioles*.—
*Length*.—About 1.5 mm.
*Diameter*.—About 2 mm.
*Strength*.—Moderately strong.
*Texture and luster, upper surface*.—Smooth, glabrous; slightly glossy.
*Texture and luster, lower surface*.—Smooth, glabrous: moderately glossy.
*Color, upper surface*.—Close to 152A to 152B.
*Color, lower surface*.—Close to 144B; at the proximal end, close to 144A.

Flower description:
*Flower type and flowering habit*.—Single salverform flowers arranged singly or in terminal or axillary cymes; flowers star-shaped and face mostly outwardly to slightly nodding or slightly upright; freely flowering habit with about 18 flower buds and flowers develop per plant during the flowering season.
*Natural flowering season*.—Plants flower continuously from spring into the autumn in Spain; early flowering habit, plants in full flower about six to seven months after planting.
*Flower longevity on the plant*.—About ten days; flowers not persistent.
*Fragrance*.—None detected.
*Inflorescence height*.—About 10.1 cm.
*Inflorescence diameter*.—About 7 cm.
*Flower buds*.—
*Length*.—About 5.5 cm.
*Diameter*.—About 1.2 cm.
*Shape*.—Narrowly oblanceolate.
*Texture and luster*.—Smooth, glabrous; slightly to moderately glossy.
*Color*.—Distally, close to 51C to 51D; mid-section, close to 145C tinged with close to 56B and 56C; proximally, close to 145A.
*Flowers*.—
*Appearance*.—Flared trumpet, corolla fused and five-parted.
*Diameter*.—About 5.7 cm.
*Depth* (*length*).—About 5 cm.
*Throat diameter*.—About 1.3 cm.
*Tube length*.—About 4.2 cm.
*Tube diameter*.—Distally, about 1.7 cm; proximally, about 3.5 mm.
*Petals*.—
*Quantity and arrangement*.—Five petals arranged in a single whorl; lower 64% portion of the petals are fused into a funnelform tube.
*Petal length*.—About 6.6 cm.
*Petal width*.—About 2.4 cm.
*Petal shape and appearance*.—Unequal spatulate; slightly convex and moderately reflexed.
*Petal apex*.—Short unequal apiculate.
*Petal margin*.—Entire; moderately undulate.
*Petal texture and luster, upper surface*.—Smooth, glabrous; not rugose; velvety; slightly glossy.
*Petal texture and luster, lower surface*.—Smooth, glabrous; not rugose; slightly velvety; slightly glossy.
*Throat texture*.—Smooth, glabrous; velvety.
*Tube texture*—Smooth, glabrous; slightly velvety.
*Color*.—
*Petal, when opening, upper surface*.—Close to 58B.
*Petal, when opening, lower surface*.—Close to 54C; apex, close to N155A; towards the base, close to 158B.
*Petal, fully opened, upper surface*.—Close to N66A slightly tinged with close to 58B; towards the margins, close to N66B; towards the throat, close to 8C; venation, similar to lamina color; main color becoming closer to 61C with subsequent development.
*Petal, fully opened, lower surface*.—Close to 64D; venation, close to 69D; color becoming closer to 61D with subsequent development.
*Throat*.—Distally, close to 14B and proximally, close to 14C; at the base, close to 145B; venation, similar to lamina colors.
*Tube*.—Close to 51D; towards the base, tinged with close to 150D and at the base, close to 150A; venation, similar to lamina.
*Sepals*.—
*Quantity and arrangement*.—Five sepals arranged in a single whorl.
*Calyx length*.—About 6.5 mm.
*Calyx diameter*.—About 4 cm.
*Sepal length*.—About 6.5 mm.
*Sepal width*.—About 1 mm.
*Sepal shape*.—Lanceolate.
*Sepal apex*.—Narrowly acuminate.
*Sepal base*.—Broadly cuneate; fused at the base.
*Sepal margin*.—Entire.
*Sepal texture and luster, upper surface*.—Smooth, glabrous; moderately glossy.
*Sepal texture and luster, lower surface*.—Smooth, glabrous; matte.
*Sepal color:*—
*When opening, upper surface*.—Close to 145B; at the apex, close to 176B.

*When opening, lower surface*.—Close to 144C; towards the base, close to 144A; at the apex, close to 176B.
*Fully opened, upper surface*.—Close to 145B; at the apex, close to 176B.
*Fully opened, lower surface*.—Close to 144C; towards the base, close to 144B to 144C; at the apex, close to 176B.
*Peduncles*.—
*Length*.—About 5.3 cm.
*Diameter*.—About 2 mm.
*Strength*.—Strong.
*Aspect*.—About 60° from stem axis.
*Texture and luster*.—Smooth, glabrous; slightly to moderately glossy.
*Color*.—Close to 143C.
*Pedicels*.—
*Length*.—About 1 cm.
*Diameter*.—About 2 mm.
*Strength*.—Strong.
*Aspect*.—About 20° from peduncle axis.
*Texture and luster*.—Smooth, glabrous; slightly glossy.
*Color*.—Close to 145A.
*Reproductive organs*.—
*Stamens*.—
*Quantity and arrangement*.—Typically five; basifixed; anthers connivent.
*Filament length*.—About 2 mm.
*Filament color*.—Close to 150D.
*Anther size*.—About 1.5 mm by 8 mm.
*Anther shape*.—Narrowly oblong.
*Anther color*.—Close to 162C.
*Pollen amount*.—None observed.
*Pistils*.—
*Quantity*.—Typically one.
*Pistil length*.—About 1.7 cm.
*Style length*.—About 1.5 cm.
*Style color*.—Close to 145 C.
*Stigma diameter*.—About 1.75 mm.
*Stigma shape*.—Club-shaped, pointed.
*Stigma color*.—Close to 151D.
*Ovary color*.—Close to 143B.
*Seeds and fruits*.—To date, seed and fruit production have not been observed on plants of the new *Mandevilla*.

Pathogen & pest resistance:
To date, plants of the new *Mandevilla* have not been noted to be resistant to pathogens and pests common to *Mandevilla* plants.

Temperature tolerance:
Plants of the new *Mandevilla* have been observed to tolerate temperatures of about 5° C. to 40° C. and to be suitable for USDA Hardiness Zones 9 through 13.

It is claimed:

1. A new and distinct *Mandevilla* plant named 'Lannorthdakota' as illustrated and described.

* * * * *